United States Patent [19]

Kurahashi et al.

[11] Patent Number: 4,998,018

[45] Date of Patent: Mar. 5, 1991

[54] TWO-WAVELENGTH TYPE RESPIRATORY GAS CONCENTRATION MEASURING APPARATUS

[75] Inventors: Muneshige Kurahashi, Tokorozawa; Naoki Kato, Tokyo, both of Japan

[73] Assignee: Nihon Kohden Corporation, Tokyo, Japan

[21] Appl. No.: 483,914

[22] Filed: Feb. 22, 1990

[30] Foreign Application Priority Data

Mar. 1, 1989 [JP] Japan .................................. 1-46649

[51] Int. Cl.$^5$ ........................... G01J 5/58; G01J 5/10; G01J 1/00
[52] U.S. Cl. .................................. 250/343; 250/341; 250/339
[58] Field of Search ...................... 250/339, 343, 341; 356/437

[56] References Cited

U.S. PATENT DOCUMENTS

| | | | |
|---|---|---|---|
| 4,067,320 | 1/1978 | Olsson et al. | 250/343 X |
| 4,314,564 | 2/1982 | Albarda | 250/343 X |
| 4,522,204 | 6/1985 | Kurahashi et al. | 250/343 X |
| 4,587,427 | 5/1986 | Talbot et al. | 250/339 |
| 4,914,720 | 4/1990 | Knodle et al. | 250/343 |

Primary Examiner—Constantine Hannaher
Assistant Examiner—Edward J. Glick
Attorney, Agent, or Firm—Hoffman & Baron

[57] ABSTRACT

A two-wavelength type respiratory gas concentration measuring device includes a connector tube which is held in the mouth of an examinee and which has airtight windows, a light source which applies infrared rays through the windows of the connector tube, and first and second filters. The first filter allows the transmission of a light component whose wavelength is such that it is absorbed by the respiratory gas, and the second filter allows the transmission of a light component whose wavelength is such that it is not absorbed by the respiratory gas. A photodetector converts the infrared rays transmitted through the filters into an electric signal. A first detector receives the electric signal and detects the light output of the first filter. A second detector receives the electric signal and detects the light output of the second filter. A power computing circuit performs a power computation of the output of the second detector with a power exponent m. A divider circuit divides the output of the first detector by the output of the first power computing circuit. A DC level detector detects the DC level of the photodetector when no infrared rays are applied. A second power computing circuit performs a power computation of the output of the DC-level detector with a power exponent of $2(m-1)$. A multiplier circuit multiplies the output of the second power computing circuit by the output of the divider.

2 Claims, 3 Drawing Sheets

TWO-WAVELENGTH TYPE RESPIRATORY GAS CONCENTRATION MEASURING APPARATUS

BACKGROUND OF THE INVENTION

1. Field of the Invention

The present invention relates to a respiratory gas concentration measuring apparatus for measuring the concentrations of a gas, such as $CO_2$, in respiratory gas based on the absorption of gases to be measured with respect to light of a particular wavelength which passes therethrough.

2. Description of the Prior Art

U.S. Pat. No. 4,522,204, the disclosure of which is incorporated herein by reference, describes a two-wavelength type respiratory gas concentration measuring apparatus in which infrared light rays are generated to pass transversely through a tube through which respiratory gas passes longitudinally. Two different filters are alternately positioned in the light path. The filters are situated so that the tube containing the respiratory gas is located between the light source and the filters. One of the filters allows the transmission of a light component whose wavelength will be absorbed by a particular gas, while the other filter allows the transmission of a light component whose wavelength will not be absorbed by the same gas. The infrared rays transmitted through these filters are detected by a photodetector employing a PbSe infrared-ray sensor.

The photodetector provides an output signal corresponding to the light transmitted through each filter to a first and a second detector. Based on the signal from the photodetector, the first detector effectively detects the light output of the filter which allows the transmission of the absorption wavelength light component, and the second detector effectively detects the light output of the filter which allows the transmission of the non-absorption wavelength light component. The concentration of a gas, such as $CO_2$, contained in a respiratory gas is measured on the basis of the ratio of the outputs of the two detectors.

Based upon the ratio between the output Vs of the first detector, which detects the absorbed wavelength light component, and the output Vc of the second detector, which detects the non-absorbed wavelength light component, (i.e., Vs/Vc), an apparatus as described above makes it possible to obtain a gas concentration measurement in which errors due to variations in the intensity of the light source and in the sensitivity of the measuring devices are compensated for. However, if temperature-dependent coefficients of the detected outputs dependent on light rays of the different wavelengths (absorbed wavelength and unabsorbed wavelength) are different from each other due to variations in temperature or the characteristics of the infrared-ray detecting element, temperature dependent drifts will still occur.

In view of the above, the applicants of the present application have proposed in U.S. Pat. No. 4,522,204 a two-wavelength type respiratory gas concentration measuring apparatus. This instrument was based on the finding that the temperature-dependent drifts in detector outputs due to the components of the apparatus from the light source to the first and second detectors have an exponential relationship to temperature-dependent coefficients inherent in the wavelengths at least in the temperature range of 10° C. to 40° C. The proposed apparatus is equipped with a power computing means. Assuming the temperature-dependent coefficient of the first detector output is $\theta 1$ and the temperature-dependent coefficient of the second detector output is $\theta 2$, the power computing means calculates $Vs/Vc^m$ (where $m=\theta 1/\theta 2$). This computation eliminates any influence due to the difference in the temperature-dependent coefficients.

Applicants of the present application have also proposed in co-pending U.S. application Ser. No. 07/462,228, filed Jan. 9, 1990, the disclosure of which is also incorporated herein by reference, a photodetector having a PbSe infrared-ray sensor in which the effect of the temperature fluctuation on the dark resistance of the PbSe infrared-ray sensor is taken into account. Thus, instead of providing a conventional constant-current type photodetector, a constant-voltage type photodetector is used in which the current that flows when a constant voltage Vx is applied to the PbSe infrared-ray sensor 41 is measured, as shown in FIG. 3, thereby making it possible to obtain an excellent temperature compensation characteristic.

Thus, assuming the voltage of the constant-voltage source is Vx, the variation in resistance when the PbSe infrared-ray sensor 41 receives infrared rays is $\Delta R$, and its dark resistance is Rd, the A.C. infrared-ray-detection signal Iout (AC) will be as follows:

$$I_{out}(AC) = \frac{Vx}{Rd - \Delta R} - \frac{Vx}{Rd} \approx \frac{\Delta R \cdot Vx}{Rd^2} \quad (\Delta R << Rd)$$

Thus, it is ascertained that the temperature-dependent coefficient of $\Delta R$ corresponds, at least at normal temperatures, approximately to the square of the temperature-dependent coefficient of Rd. Since the temperature-dependent coefficient of $\Delta R/Rd^2$ is approximately 0, this makes it possible to output an infrared-ray-detection signal which is determined by a Vx that is stable with respect to temperature. Assuming the resistance of a feedback resistor 42 is Rf, the A.C. voltage infrared-red-detection signal Vout (AC) will be as follows:

$$V_{out}(AC) = \frac{Vx \cdot Rf}{Rd - \Delta R} - \frac{Vx \cdot Rf}{Rd} \approx \frac{\Delta R \cdot Vx \cdot Rf}{Rd^2} \quad (1)$$

Thus, an infrared-ray-detection signal which is more stable with respect to fluctuations in temperature can be obtained.

However, when a constant-voltage type infrared detector, such as disclosed in U.S. application Ser. No. 07/462,228 mentioned previously, is used in a two-wavelength type respiratory gas concentration measuring apparatus, such as described in U.S. Pat. No. 4,522,204, it is not sufficient to use just the compensation technique provided by the power computation circuit disclosed in the aforementioned U.S. patent, as that technique was more specifically designed for use with a respiratory gas concentration measuring apparatus employing a constant-current type photodetector.

OBJECTS AND SUMMARY OF THE INVENTION

It is an object of the present invention to compensate for calculation errors due to the difference in temperature-dependent coefficients between the gas-absorption-wavelength detector and the non-absorption-wavelength detector in a two-wavelength type respiratory gas concentration measuring apparatus of the type using a constant-voltage type photodetector employing a PbSe infrared-ray sensor.

In accordance with one form of the present invention, a two-wavelength type respiratory gas concentration measuring apparatus includes a connector tube equipped with an open tube end to be held in the mouth of an examinee and an opposite open end and airtight windows provided between both ends of the connector tube. A light source is adapted to apply infrared rays in a path passing transversely through said connector tube by way of the windows. A chopper has first and second filters situated thereon and is adapted to alternately position in the light path the first filter which allows the transmission of a light component whose wavelength is such that it is absorbed by a particular gas and the second filter which allows the transmission of a light component whose wavelength is such that it is not absorbed by the particular gas. A photodetector is included and has a PbSe infrared-ray sensor adapted to convert the infrared rays transmitted through the filters to an electric signal by means of the PbSe infrared-ray sensor. Also included is a first detector adapted to detect the output of the first filter from said electric signal, and a second detector adapted to detect the output of said second filter from the electric signal.

The apparatus further includes a first power computing circuit adapted to perform the power computation of the output of the second detector with a power exponent m, and a divider circuit for dividing the output of the first detector by the output of the first power computing circuit. A DC level detector is provided for determining the DC level of said photodetector when no infrared rays are applied. A second power computing circuit performs the power computation of the output of the DC-level detector with a power exponent of $2(m-1)$. A multiplier circuit multiplies the output of the second power computing circuit by the output of said divider circuit.

The power component m represents the ratio of a temperature-dependent coefficient $\alpha_1$, with respect to the incident light quantity of the light component of the infrared rays whose wavelength is absorbed by the particular gas, of the variation in resistance, which exponentially fluctuates with respect to temperature changes, of the PbSe infrared-ray sensor to a temperature-dependent coefficient $\alpha_2$, with respect to the incident light quantity of the light component of the infrared rays whose wavelength is not absorbed by the same particular gas, of the variation in resistance, which exponentially fluctuates with respect to temperature changes, of the PbSe infrared-ray sensor, whereby the power exponent m and the temperature-dependent coefficients $\alpha_1$ and $\alpha_2$ are in the relationship:

$$m = \frac{\alpha_1}{\alpha_2}$$

The photodetector circuit supplies a constant voltage to the PbSe infrared-ray sensor, and detects the current flowing through the infrared-ray sensor as an infrared-ray detection signal.

In accordance with this invention, the above-described constant-voltage type photodetector employing a PbSe infrared-ray sensor can perform gas-concentration measurements with more accuracy and can compensate for errors due to the exponential temperature-dependent characteristics of both detectors. Therefore, this apparatus achieves a more accurate gas concentration measurement than the constant-current type photodetector.

These and other objects, features and advantages of this invention will be apparent from the following detailed description of illustrative embodiments thereof, which is to be read in connection with the accompanying drawings.

DETAILED DESCRIPTION OF THE PREFERRED EMBODIMENTS

Figure 1:
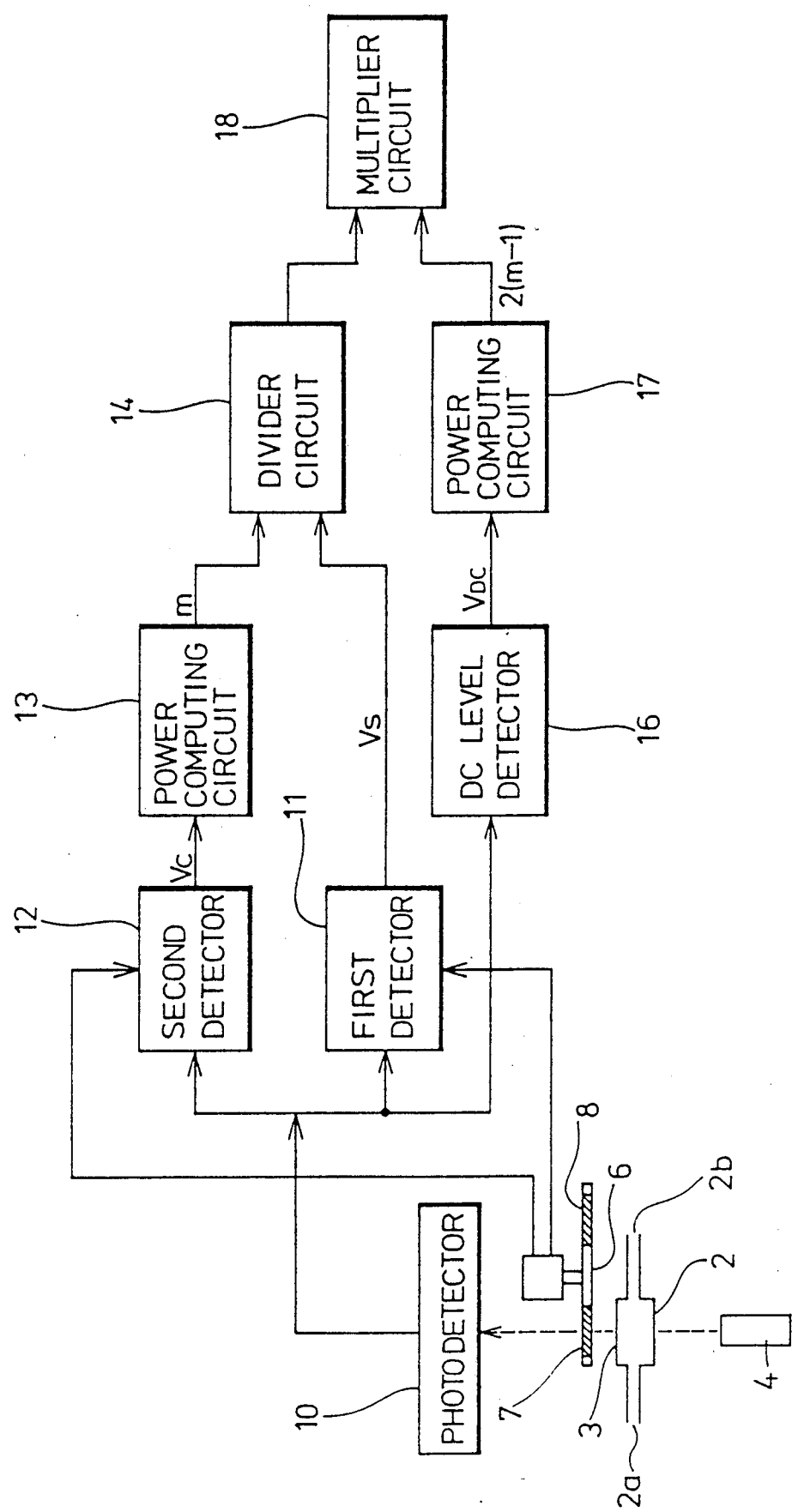
FIG. 1 is a diagram showing the circuit configuration of a two-wavelength type gas concentration measuring apparatus in accordance with an embodiment based on the principle of this invention.

The embodiment shown in FIG. 1 illustrates the principle of this invention. As shown in the drawing, the two-wavelength type respiratory gas concentration measuring apparatus of this invention comprises: a connector tube 2 having a tube end 2a to be held in the mouth of an examinee and an opposite open end 2b; airtight windows 3 provided between both sides of the connector tube 2; a light source 4 adapted to apply infrared light rays that pass transversely through the connector tube 2 by way of the windows 3; a chopper 6 adapted to alternately position in the light path a first filter 7 which allows the transmission of a light component whose wavelength is such that it is absorbed by a particular gas and a second filter 8 which allows the transmission of a light component whose wavelength is such that it is not absorbed by the same gas; a photodetector 10 for converting the infrared rays which permeate the filters into an electric signal by means of a PbSe infrared-ray sensor; first detector 11 which receives the electric signal from the sensor and which is adapted to effectively detect the amount of light passing through filter 7; a second detector 12 which also receives the electric signal from the sensor and which is adapted to effectively detect the amount of light passing through filter 8; a power computing circuit 13 adapted to perform a power computation of the output of the second detector 12 with a power exponent m; a divider circuit 14 for dividing the output of the first detector 11 by the output of the power computing circuit 13; a DC level detector 16 for determining the DC level of the photodetector 10 when no infrared rays are detected; a power computing circuit 17 for performing a power computation of the output of the DC level detector 16 with a power exponent $2(m-1)$; and a multiplier circuit 18 for multiplying the output of this power computing circuit 17 by the output of the divider circuit 14. Here, m represents the ratio of the temperature-dependent coefficients $\alpha_1$ and $\alpha_2$ which correspond to the first and second detectors, respectively. The coefficients are computed from the exponential variations in resistance of the PbSe infrared-ray sensor with respect to changes in temperature.

Thus, $m = \dfrac{\alpha_1}{\alpha_2}$

The photodetector 10 supplies a constant voltage to the PbSe infrared-ray sensor while detecting the current flowing through this infrared-ray sensor as a detection signal.

It is well known that an apparatus of this type performs gas concentration measurements by means of a photosensor and calculated according to the Lambert-Beer law:

$$V_{so} = V_o e^{-kc} \qquad (2)$$

where Vso is the photoelectric conversion output; Vo is Vso when the gas concentration is 0; K is a proportionality constant; and C is the gas concentration.

Figure 4:
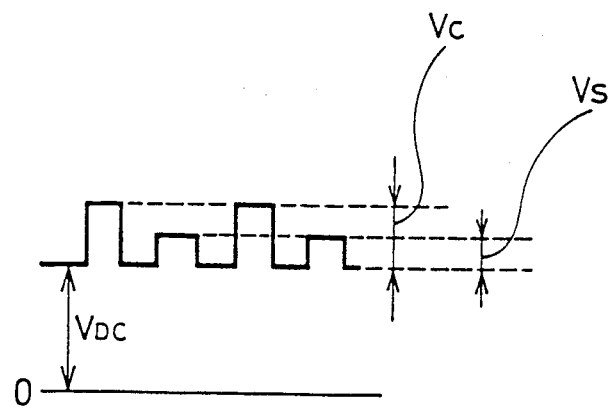
FIG. 4 is a diagram showing the output waveform of the photodetector of this invention.

Thus, the output Vs of the first detector 11 and Vc of the second detector 12 can be expressed with respect to the gas concentration as follows (see FIG. 4):

$$V_s = \dfrac{\Delta R_{so} \cdot \exp(-\alpha_1 T)}{\{R_{do} \cdot \exp(-\alpha_3 T)\}^2} \cdot V_x \cdot R_f \cdot \exp(-KC) \qquad (3)$$

$$V_c = \dfrac{\Delta R_{co} \cdot \exp(-\alpha_2 T)}{\{R_{do} \cdot \exp(-\alpha_3 T)\}^2} \cdot V_x \cdot R_f \qquad (4)$$

where $\Delta R_{so}$ represents the variation in resistance at 0° C. of the PbSe infrared light sensor with respect to the incident infrared-ray component of the absorption wavelength, and $\Delta R_{co}$ represents the variation in resistance at 0° C. of the PbSe infrared light sensor with respect to the incident infrared-ray component of the non-absorption wavelength. The Rdo in the above equations represents the dark resistance at 0° C. of the PbSe infrared-ray sensor, and $\exp(-\alpha_1 T)$, $\exp(-\alpha_2 T)$ and $\exp(-\alpha_3 T)$ respectively represent the temperature-dependent drift coefficients which are generated as exponential functions of the temperature-dependent coefficients $\alpha_1$, $\alpha_2$ and $\alpha_3$ corresponding to $\Delta R_{so}$, $\Delta R_{co}$ and $\Delta R_{do}$. Vc is independent of the gas concentration.

Accordingly, using the above values, the output of the divider circuit 14 is:

$$\dfrac{V_s}{V_c^m} = \dfrac{\Delta R_{so}}{\Delta R_{co}^m} \cdot \qquad (5)$$

$$\{R_{do} \cdot \exp(-\alpha_3 T)\}^{2(m-1)} \cdot V_x^{(1-m)} \cdot R_f^{(1-m)} \cdot \exp(-kc)$$

Figure 3:
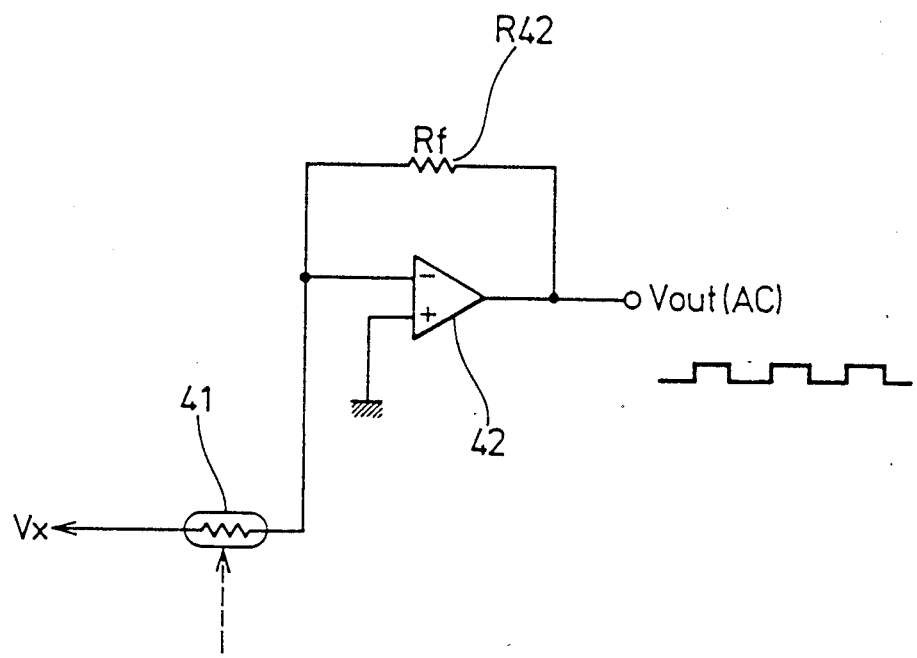
FIG. 3 is a circuit diagram of the photodetector in the embodiment of FIG. 2.

The D.C. voltage level when no infrared rays are detected by the PbSe photodetector of FIG. 3 is as follows (see FIG. 4):

$$V_{DC} = \dfrac{V_x \cdot R_f}{R_{do} \cdot \exp(-\alpha_3 T)} \qquad (6)$$

Therefore, the output of the multiplier circuit 18 is:

$$\dfrac{V_s}{V_c^m} \cdot V_{DC}^{2(m-1)} = \dfrac{\Delta R_{so}}{\Delta R_{co}^m} \cdot (V_x \cdot R_f)^{(m-1)} \cdot \exp(-kc) \qquad (7)$$

Thus, by performing the well-known proportional calculation of the detection outputs (using the Lambert-Beer Law), the fluctuation in the intensity of the infrared light source and the sensitivity of the PbSe infrared-ray sensor are compensated for. In addition, the temperature-dependent coefficients of the PbSe infrared light sensor are compensated for by the D.C. level of the photodetector 10 in the state where it detects no infrared light.

Figure 2:
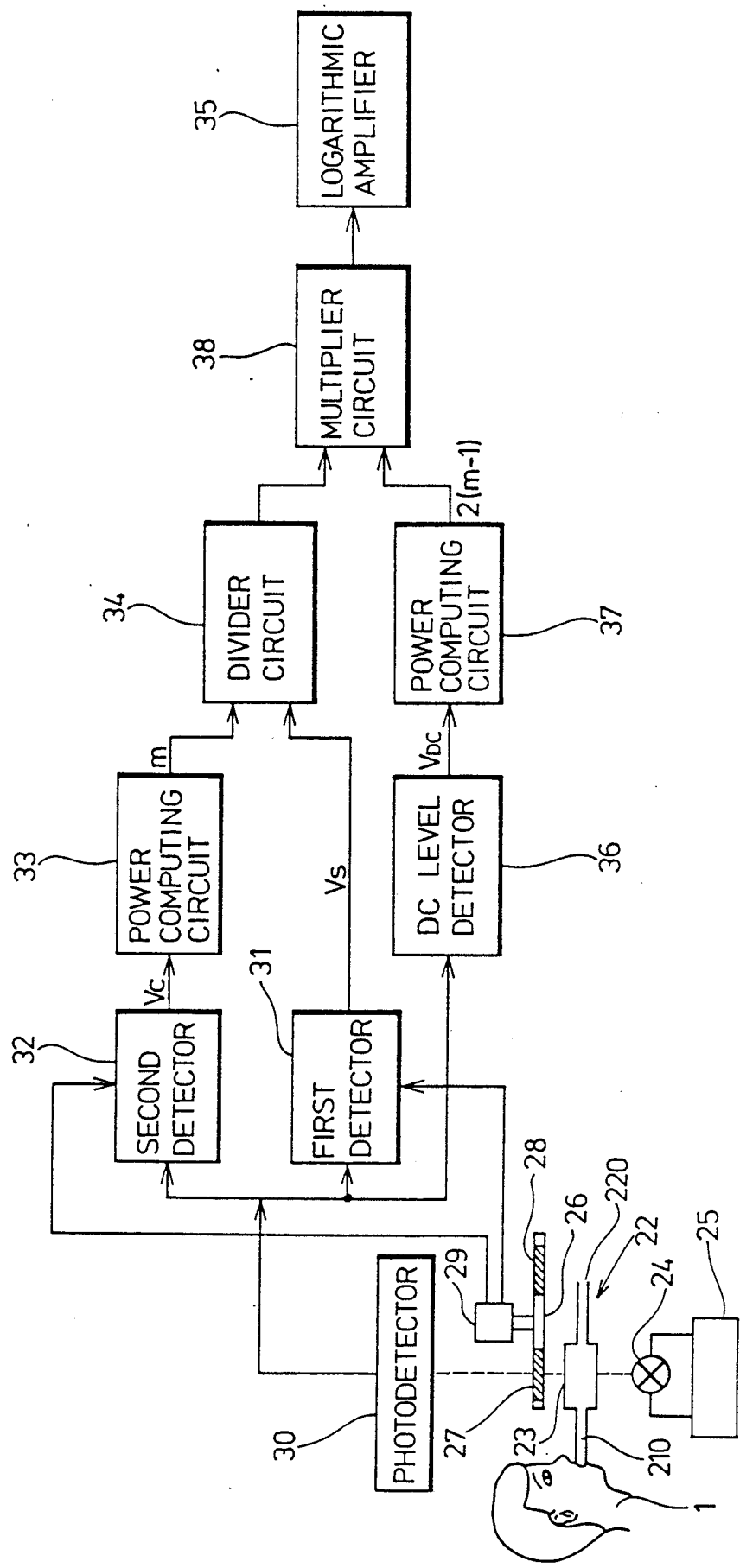
FIG. 2 is a diagram showing the circuit configuration of a two-wavelength type gas concentration measuring apparatus in accordance with a more specific embodiment of this invention.

FIG. 2 shows a more specific embodiment of this invention as a two-wavelength type respiratory gas concentration measuring apparatus which utilizes infrared light to measure the concentration of $CO_2$. The apparatus shown comprises a connector tube 22 equipped with a tube end 210 to be held in the mouth of an examinee 1, an opposite open end 220 to be vented to the atmosphere or connected to an artificial respiratory system, an anesthetizer or the like, and a pair of intermediate windows 23. The intermediate windows 23 are located at central portions of the connector tube 22 and are kept airtight by transparent sapphire or the like. The apparatus further comprises an infrared light source 24, a power source 25, and a rotatable chopper 26.

The chopper 26 has a pair of filters 27 and 28 disposed in diametrically opposite relation. The filter 27 allows the transmission of only the light component whose wavelength is such that it is absorbed by $CO_2$ gas, whereas the filter 28 allows the transmission of only the light component whose wavelength is such that it is not absorbed by $CO_2$ gas. The chopper 26 is rotated at a constant cyclic period by a motor 29. A photodetector 30 serves to convert the quantity of irradiated light to an electric signal. The output of the photodetector 30 is supplied to a first detector 31, a second detector 32 and a DC level detector 36.

The first detector 31 detects the output of photodetector 30 when filter 27 is positionally aligned with the infrared light path passing transversely through the windows 23, as shown in the drawing. The second detector 32 serves to detect the output of photodetector 30 when filter 28 is positionally aligned with windows 23 and the infrared light path. The apparatus shown further comprises a power computing circuit 33 for raising the output Vc of the second detector 32 to the m-th power, a divider circuit 34 for dividing the output Vs of the first detector by the value $V_c^m$ obtained by circuit 33, and a logarithmic amplifier 35 adapted to logarithmically convert the input signal and to output a $CO_2$ concentration signal.

There is also a DC-level detector circuit 36 adapted to detect the DC-signal level when no infrared rays are applied to the photodetector 30, a power computing circuit 37 for performing the power computation of the detection output $V_{dc}$ of the DC-level detector circuit 36 with a power exponent $2(m-1)$, and a multiplier circuit 38 for multiplying the output of the divider circuit 34 by the output of the power computing circuit 37. As shown in FIG. 3, the photodetector 30 is of a constant-voltage type equipped with an operational amplifier 42.

The power computing circuits 33 and 37 may consist of power computing amplifiers adapted to perform analog computation. Alternatively, the respective outputs of the detectors 31, 32 and the DC-level detector 36 may be analog/digital-converted and undergo an operating process performed by a computer. The power exponent m may be calculated from the temperature-dependent coefficients $\alpha_1$, $\alpha_2$ and $\alpha_3$ which are detected on the basis of the temperature-dependent fluctuations in the outputs of detectors 31, 32 and DC-level detector 36, respectively. Alternatively, the power exponent m may be kept variable in the power computing circuits 33 and 37 and determined through experiment at an optimum value. It has been determined that the power exponent for a $CO_2$ measurement is normally in the range of 1.1 to 1.2. Since the wavelength of the infrared rays varies with the gas to be measured, the power exponent m must be determined every time a different type of gas is to be measured.

When measuring the $CO_2$ concentration in the respiratory gas of an examinee 1, the connector tube 2 is held in the mouth of the examinee before exhaling. As a result, the first detector 31 generates an output $V_s$ which corresponds to the $CO_2$ concentration and which is to be expressed by the equation (3). This output $V_s$ drifts due to variations in temperature as an exponential function of a coefficient $(\alpha_1 - 2\alpha_3)$. At the same time, the second detector 32 generates an output $V_c$ which is determined by a reference voltage irrespective of the $CO_2$ concentration, i.e., in accordance with equation (4) and which likewise drifts as an exponential function of a coefficient $(\alpha_2 - 2\alpha_3)$. This output $V_c$ is raised to the m-th power by the power computing circuit 33, causing an output voltage corresponding to $V_c^m$ to be generated. Then, the divider circuit 34 computes $V_s/V_c^m$ as indicated by equation (5).

The DC level-detector 36 determines the DC-signal level $V_{dc}$ when the photodetector 30 receives no infrared rays, causing the power computing circuit 37 to perform the power computation of $V_{dc}^{2(m-1)}$. The multiplier circuit 38 performs the multiplication of equation (7) by obtaining the product of the output from the divider circuit 34 and the output of the power computing circuit 37. The output of the multiplier circuit 38 is supplied to the logarithmic amplifier 35 which outputs a $CO_2$ gas concentration signal which is a voltage that is proportional to the $CO_2$ concentration.

If desired, the + input terminal of the operational amplifier 42 in the embodiment shown in FIG. 3 may not be grounded. It is also possible to apply the + input terminal to a circuit to which a constant D.C. level is added. In addition, other types of photodetectors which have individual components, such as transistors and FETs, may be used instead of an operational amplifier.

Although illustrative embodiments of the present invention have been described herein with reference to the accompanying drawings, it is to be understood that the invention is not limited to those precise embodiments and that various other changes and modifications may be effected therein by one skilled in the art without departing from the scope or spirit of the invention.

What is claimed is:

1. A two-wavelength type respiratory gas concentration measuring apparatus comprising:
   a connector tube equipped with a tube end to be held in the mouth of an examinee and an opposite open end, and having airtight windows provided between both ends of said connector tube;
   a light source adapted to apply infrared rays in a light path passing transversely through said connector tube by way of said windows;
   a first filter which allows the transmission of a light component whose wavelength is such that it is absorbed by a particular gas of a respiratory gas breathed into the tube by the examinee;
   a second filter which allows the transmission of a light component whose wavelength is such that it is not absorbed by said particular gas;
   means for alternately positioning the first filter and the second filter in the light path;
   photodetector means for converting the infrared rays transmitted through said filters to an electric signal, the photodetector means including a PbSe infrared-ray sensor;
   first detector means for detecting the light output of said first filter from said electric signal;
   second detector means for detecting the light output of said second filter from said electric signal;
   first power computing means for performing the power computation of the output of said second detector means with a power exponent m;
   divider means for dividing the output of said first detector means by the output of said first power computing means;
   DC level detector means for detecting the DC level of said photodetector means when no infrared rays are applied thereto;
   second power computing means for performing the power computation of the output of said DC-level detector means with a power exponent of $2(m-1)$; and
   multiplier means for multiplying the output of said second power computing means by the output of said divider means;
   said power component m representing the ratio of a temperature-dependent coefficient $\alpha_1$, with respect to the incident light quantity of the light component of the infrared rays whose wavelength is absorbed by the particular gas, of the variation with respect to temperature in resistance of the PbSe infrared-ray sensor to a temperature dependent coefficient $\alpha_2$, with respect to the incident light quantity of the light component of the infrared rays whose wavelength is not absorbed by the particular gas, of the variation with respect to temperature in resistance of the PbSe infrared-ray sensor, whereby said power exponent m and said temperature-dependent coefficients $\alpha_1$ and $\alpha_2$ are in the relationship:

$$m = \frac{\alpha_1}{\alpha_2}$$

said photodetector means supplying a constant voltage to said PbSe infrared-ray sensor, and detecting the current flowing through said infrared-ray sensor as an infrared-ray detection signal.

2. A two-wavelength type respiratory gas concentration measuring apparatus comprising:
   a connector tube equipped with an open tube end to be held in the mouth of an examinee and an opposite open end and airtight windows provided between both ends of said connector tube;
   a light source adapted to apply infrared rays in a path passing transversely through said connector tube by way of said windows;
   a chopper having first and second filters situated thereon and adapted to alternately position in said light path the first filter which allows the transmission of a light component whose wavelength is such that it is absorbed by a particular gas and the second filter which allows the transmission of a light component whose wavelength is such that it is not absorbed by said particular gas;
   a photodetector including a PbSe infrared-ray sensor adapted to convert the infrared rays transmitted through said filters to an electric signal by means of the PbSe infrared-ray sensor;

a first detector adapted to detect the output of said first filter from said electric signal;

a second detector adapted to detect the output of said second filter from said electric signal;

a first power computing circuit adapted to perform the power computation of the output of said second detector with a power exponent m;

a divider circuit for dividing the output of said first detector by the output of said first power computing circuit;

a DC level detector for determining the DC level of said photodetector when no infrared rays are applied;

a second power computing circuit for performing the power computation of the output of said DC-level detector with a power exponent of 2(m−1); and a multiplier circuit for multiplying the output of said second power computing circuit by the output of said divider circuit;

said power component m representing the ratio of a temperature-dependent coefficient $\alpha_1$, with respect to the incident light quantity of the light component of the infrared rays whose wavelength is absorbed by the particular gas, of the variation in resistance, which exponentially fluctuates with respect to temperature changes, of the PbSe infrared-ray sensor to a temperature-dependent coefficient $\alpha_2$, with respect to the incident light quantity of the light component of the infrared rays whose wavelength is not absorbed by the same particular gas, of the variation in resistance, which exponentially fluctuates with respect to temperature changes, of the PbSe infrared-ray sensor, whereby said power exponent m and said temperature-dependent coefficients $\alpha_1$ and $\alpha_2$ are in the relationship:

$$m = \frac{\alpha_1}{\alpha_2}$$

said photodetector circuit supplying a constant voltage to said PbSe infrared-ray sensor, and detecting the current flowing through said infrared-ray sensor as an infrared-ray detection signal.

* * * * *